United States Patent [19]
Kishner

[11] 4,076,421
[45] * Feb. 28, 1978

[54] SPECTROPHOTOMETER WITH PARALLEL SENSING

[75] Inventor: Stanley J. Kishner, Pomona, N.Y.

[73] Assignee: Kollmorgen Technologies Corporation, Dallas, Tex.

[*] Notice: The portion of the term of this patent subsequent to May 10, 1994, has been disclaimed.

[21] Appl. No.: 722,581

[22] Filed: Sep. 13, 1976

Related U.S. Application Data

[63] Continuation-in-part of Ser. No. 669,592, March 23, 1976, Pat. No. 4,022,534.

[51] Int. Cl.² ............................................. G01J 3/42
[52] U.S. Cl. ................................... 356/96; 356/210; 356/236
[58] Field of Search ................ 356/83, 84, 96, 97, 356/209, 210, 211, 212, 236; 350/236, 293, 294, 299

[56] References Cited

U.S. PATENT DOCUMENTS

| | | | |
|---|---|---|---|
| 2,607,899 | 8/1952 | Cary et al. | 250/205 X |
| 3,810,696 | 5/1974 | Hutchins, Jr. | 356/97 |
| 3,825,322 | 7/1974 | Mast | 350/236 |
| 3,874,799 | 4/1975 | Isaacs et al. | 356/236 X |
| 3,886,331 | 5/1975 | Schierer, Jr. | 356/83 X |
| 3,973,849 | 8/1976 | Jackson et al. | 356/83 X |
| 4,022,534 | 5/1977 | Kishner | 356/210 |

Primary Examiner—F. L. Evans
Attorney, Agent, or Firm—Morgan, Finnegan, Pine, Foley & Lee

[57] ABSTRACT

A reflection spectrophotometer which illuminates a sample with flux derived from a light source, such as a pulsed xenon flashtube, divides the light diffusely reflected by the sample into its component wavelengths and simultaneously senses the energy present at each of the component wavelengths.

9 Claims, 2 Drawing Figures

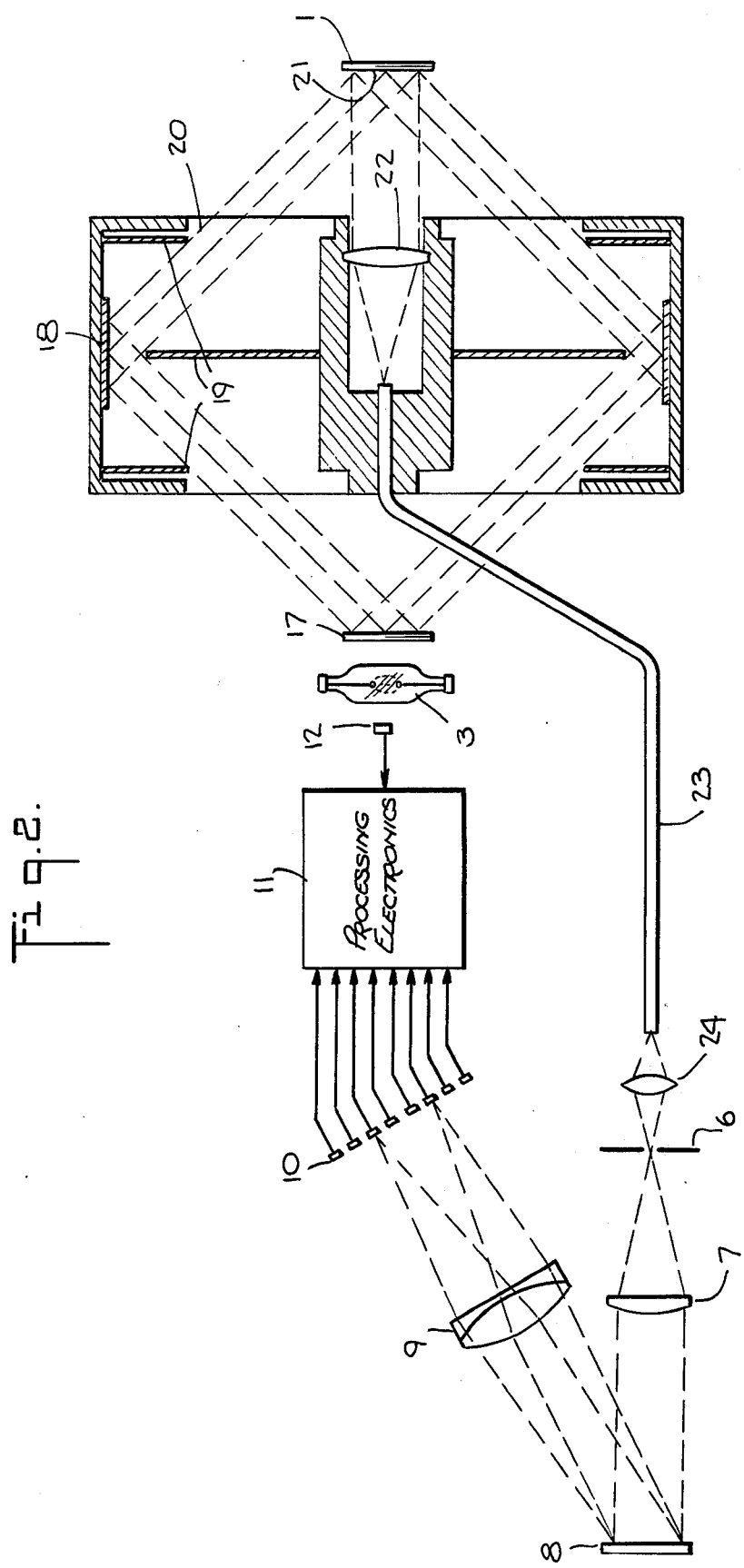

SPECTROPHOTOMETER WITH PARALLEL SENSING

This application is a continuation-in-part of my earlier application Ser. No. 669,592 filed Mar. 23, 1976 now U.S. Pat. No. 4,022,534 and entitled REFLECTOMETER OPTICAL SYSTEM.

BACKGROUND AND BRIEF DESCRIPTION OF THE INVENTION

The present invention relates generally to spectrophotometers, which are optical instruments that measure the amount of light transmitted or reflected by a sample as a function of the wavelength of the light. Radiometers, on the other hand, measure the radiation emitted by a source, with no intervening sample.

While the optical configuration of a spectrophotometer can take many forms, all current spectrophotometers have one property in common—serial scanning of wavelength. This function is carried out in the monochromator portion of the spectrophotometer, which separates light into various wavelengths. The monochromator may be used prior to sample illumination, in which case the sample is illuminated with monochromatic light. If the monochromator is placed after the sample, the sample is illuminated with polychromatic light. This latter configuration is preferable when sample fluorescence is to be excited and measured.

The means by which the light is divided into its component wavelengths in the monochromator can include dispersive elements such as diffraction gratings and prisms, or absorptive elements such as interference filters. Division of the light into its component wavelengths is achieved in a serial or sequential fashion, whereby measurements of transmittance or reflectance are made one wavelength at a time. In certain applications this serial monochromator operation takes too much time to be of practical utility, for example, when the sample is moving so that it is available for measurement only for a short period of time. The measurement of such moving samples is required in many industrial process control applications. The ability to make rapid spectrophotometric measurements could be of considerable value in these areas.

The present invention relates to a new type of spectrophotometer that measures sample transmittance or reflectance at multiple wavelengths simultaneously. The spectrophotometer of the present invention illuminates a sample with flux derived from a light source, such as a pulsed xenon flashtube, divides the light reflected or transmitted by the sample into its component wavelengths and simultaneously senses the energy present in each of the component wavelengths. Thus, spectrophotometric measurements can be made rapidly, since there is no need to sequentially scan through different wavelengths. In addition, the spectrophotometers of the present invention need no moving parts.

BRIEF DESCRIPTION OF THE DRAWINGS

FIG. 2 is a schematic diagram of another preferred embodiment of the present invention employing 45° illumination.

DETAILED DESCRIPTION

Figure 1:
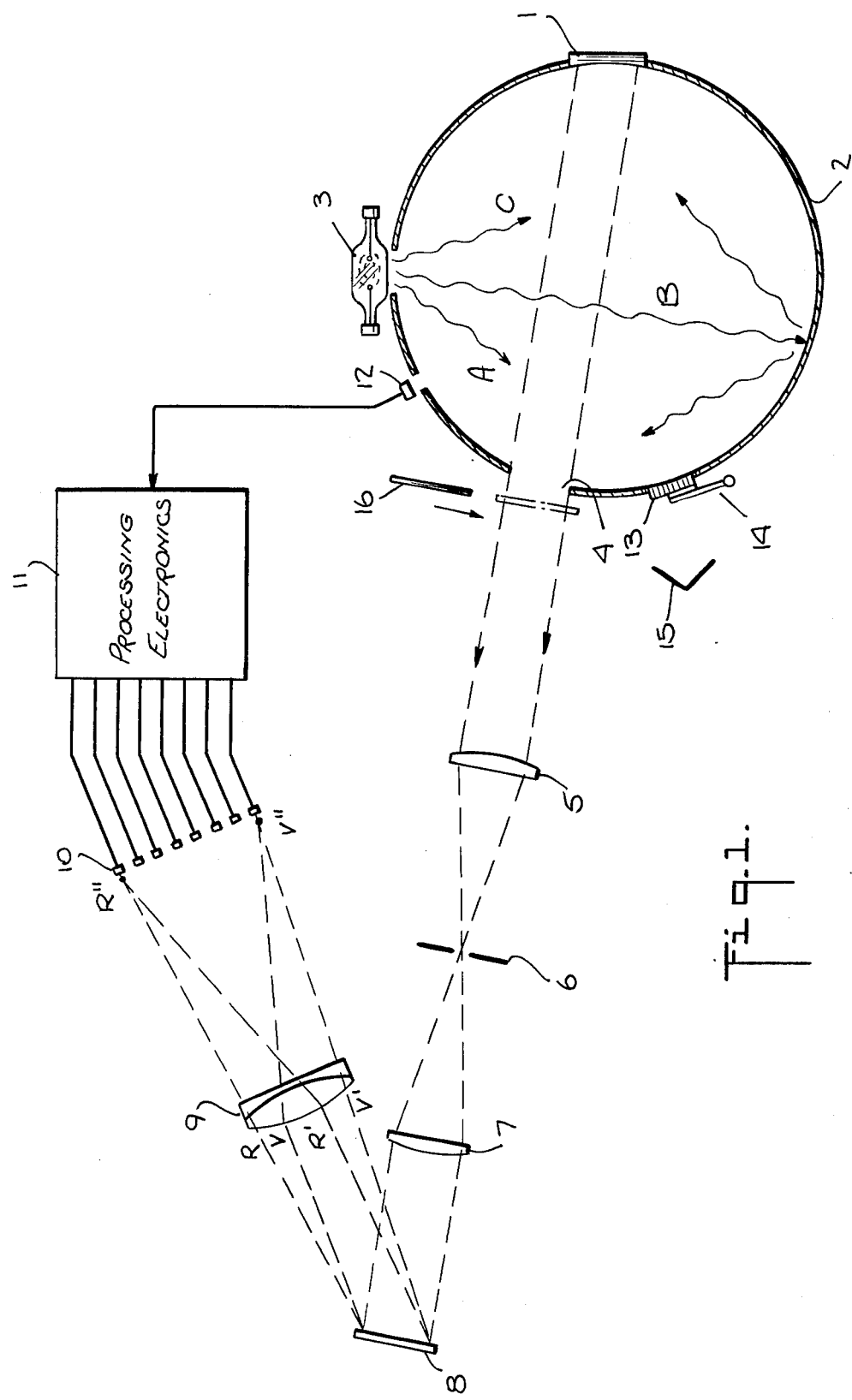
FIG. 1 is a schematic diagram of one preferred embodiment of the present invention employing integrating sphere illumination.

In the preferred embodiments of the present invention the spectrophotometer is used to make diffuse reflectance measurements throughout the visible spectrum in order to measure the color of a sample. A diagram of one preferred embodiment is shown in FIG. 1. To provide diffuse illumination a sample 1 is placed in an integrating sphere 2 which is a hollow sphere, the inside surface of which is covered with a white diffusing coating such as barium sulphate. Illumination is provided by a source of visible white light, preferably a pulsed xenon flashtube 3.

The xenon flashtube provides a short, intense pulse of illumination of approximately 10–20 microseconds duration. Because of the short duration of sample illumination it is possible to measure moving samples, which typically move a negligible distance during the measurement. (See, e.g., G. P. Bentley et al U.S. Pat. No. 3,458,261). In addition, the spectral content of the xenon flashtube is extremely stable, enabling one to compensate for flash-to-flash intensity variations using a single broadband-response photodetector. (See, e.g., P.B. Newell "Spectral Radiance and Efficiency of Pulsed Xenon Short Arcs," EG&G Tech. Report No. B-4370, March 1972). Finally, the high intensity and short pulse width renders an electronic system that is high-pass filtered extremely insensitive to the effects of ambient light.

Rays of illumination emanating from the source, such as rays A, B and C, strike the diffusely reflective wall of sphere 2 and are then diffusely reflected as, for example, is ray B. Some of these diffusely reflected rays strike the sample, but most strike another portion of the sphere a second time. This process repeats until all rays are absorbed by the sample or the sphere wall, or are reflected by the sample out of the sphere through circular aperture 4. Aperture 4 is located so as to pass rays reflected at a small angle, e.g., 8°, to the sample normal.

The rays reflected from the sample are collected by a lens 5 and focused through slit 6. The purpose of slit 6 is to restrict the angular spread of rays that proceed through the remainder of the optical system. The rays that pass through slit 6 are collimated by a lens 7 and impinge on dispersive element 8, which may be a prism or a diffraction grating. FIG. 1 illustrates a reflective diffraction grating, which is the preferred dispersive element.

Grating 8 separates the incident light into its component wavelengths by deviating each wavelength by a unique angle. For example, the red rays, which have a wavelength of 700nm, follow rays R and R', while the violet rays, which have a wavelength of 400nm, follow rays V and V'. Lens 9 focuses these rays onto a linear array of discrete photodetectors 10, the red rays being focused at point R" and the violet rays at point V". All wavelengths between 400nm and 700nm are focused at points R" and V". The result is an image of the visible spectrum in the plane of photodetector array 10.

It is possible to replace lens 7, grating 8 and lens 9 by a single diffraction grating that is manufactured on a concave spherical surface. The spherical surface behaves as a mirror with the ability to focus rays of light. The use of such a concave grating, therefore, is entirely equivalent to the use of the two lenses and the grating shown in FIG. 1. It is also possible to replace one of both of the lenses by concave mirrors, which perform the same imaging function as the lenses they replace.

In the preferred embodiment the photodetectors are silicon photodiodes. Each photodiode measures only a narrow band of wavelengths. The width of this band depends on the width of slit 6 and the width of each photodiode. The wavelengths measured depend on the positions in the array, of the detectors. The number of detectors in the array is equal to the number of different wavelengths that are simultaneously measured. In the preferred arrangement, there are 18 detectors that measure from 380nm to 720nm in equal intervals of 20nm. It has been found that the width and the center-to-center spacing of the detectors affect the accuracy of the measurements for some colors. Accordingly, the ratio of the detector width to the center-to-center detector spacing should be in the range of 0.6 to 0.9 and preferably about 0.8 for best results.

A reference photodetector 12 is located in a hole in the sphere wall in order to monitor the intensity of the illuminating pulse. The signal derived from detector 12 may be used to "normalize" the signals derived from the detectors in array 10, i.e., to compensate for fluctuations in the output intensity of xenon flashtube 3.

The signals produced by detectors 10 and 12 are transmitted to the processing electronics 11 which processes them in a manner appropriate to the particular application. This processing can involve amplification of the detected signals as well as conversion of analog signals to digital form for display of subsequent digital signal processing under the control of a suitable program. The processing electronics as such, however, form no part of the present invention.

A portion of the sphere wall, known as the specular port 13, can be removed by means of a hinge assembly 14 in order that the sample not be illuminated by rays that would be specularly reflected (i.e., reflected as off a mirror) and subsequently measured. When the specular port 13 is removed, a light trap 15 prevents light that escapes through the hole in the sphere wall from deflecting about outside the sphere. The center of the specular port is located 8° from the sample normal, so that a ray of light emanating from the specular port will be specularly reflected in such a direction that it will pass out of the sphere through aperture 4.

In order to keep the spectrophotometer in correct calibration, a prism 16 can be inserted into the path of rays that are reflected by the sample. This prism deviates rays from the sample so that they are deflected up (in a direction out of the plane of FIG. 1), thereby missing collecting lens 5. Instead, rays that are reflected from a portion of the sphere wall above the sample are directed into collection lens 5 and are analyzed. Since the reflectance of the sphere wall is quite stable from day to day, this measurement can be used as a means of periodic calibration.

A diagram of another preferred embodiment of the present invention is shown in FIG. 2, which discloses an optical system used specifically for non-contact measurements of diffuse reflectance. The source 3 first illuminates a diffusing screen 17. Light emanating from screen 17 outward at angles near 45° will enter the illumination optical system, which is circularly symmetric. The illumination system is comprised of a cylindrical reflective surface 18, preferably a mirror, which directs rays inward toward sample 1 from a complete annular ring at angles close to 45° from the sample normal. A set of baffles 19 defines the angular spread of the illumination about 45°.

The physical assembly containing the cylindrical mirror 18 and two of the baffles 19 is supported by two glass annuli 20, which also serve to protect the optical system from dust and other contaminants. The rays from cylindrical mirror 18 converge upon the sample and provide a circular spot 21 of illumination of uniform intensity. The uniformity of this spot is controlled by the degree of diffuseness of diffuser 17. The illumination spot is located outside the optical system, thereby allowing non-contact measurements to be made.

The light that is diffusely reflected by the sample is collected by a lens 22 and focused onto a fiber optic bundle 23. The bundle carries the light to the analysis portion of the optical system. A lens 24 images the light emanating from the fiber optic bundle onto the slit 6. The light then passes through elements 7, 8, 9, 10 and 11, all as previously described. Reference photodetector 12 is again located near the source 3.

The invention disclosed and claimed herein is not limited to the specific mechanism and techniques herein shown and described since modifications will undoubtedly occur to those skilled in the art. Hence, departures may be made from the form of the instant invention without departing from the principles thereof.

What I claim is:

1. A reflection spectrophotometer with parallel sensing for analyzing the light diffusely reflected by a sample comprising:
   (a) a source of white light;
   (b) means for diffusing the light emitted by said source;
   (c) illumination optics for uniformly illuminating said sample with said diffuse light from a complete annular ring at a small angular spread about 45° to said sample;
   (d) collection optics for collecting said diffuse light reflected from said sample at a small angular spread about the normal to said sample;
   (e) means for focusing the light collected by said collection optics;
   (f) a slit responsive to said focused light for restricting the angular spread thereof;
   (g) means responsive to the light passed by said slit for separating said light into its component wavelengths and for focusing the dispersed light; and
   (h) an array of discrete photodetectors located in the plane of the focused spectrum and responsive thereto for simultaneously sensing the energy present at said component wavelengths.

2. A reflection spectrophotometer according to claim 1 wherein said illumination optics comprises:
   (a) an annular reflective surface for deflecting said diffuse light toward said sample from a complete annular ring at an angular spread about 45° to said sample; and
   (b) a set of annular baffles for limiting the spread of said diffuse light to a small angle about 45° to the sample normal.

3. A reflection spectrophotometer according to claim 1 wherein said collection optics comprises:
   (a) a lens for collecting and focusing the light diffusely reflected from said sample at a small angular spread about the normal to said sample; and
   (b) a fiber optic bundle for transmitting the light collected and focused by said lens.

4. A reflection spectrophotometer according to claim 1 wherein said source of white light is a pulsed xenon flashtube.

5. A reflection spectrophotometer according to claim 4 further including a reference detector for monitoring the intensity of the illuminating pulse to compensate for fluctuations in the output intensity of said pulsed xenon flashtube.

6. A reflection spectrophotometer according to claim 1 wherein the ratio of the width of said photodetectors to the center-to-center spacing thereof is about 0.8.

7. A reflection spectrophotometer according to claim 1 wherein said means for separating said light into its component wavelengths and for focusing said dispersed light comprises:
 (a) a first lens responsive to the light passed by said slit for collimating same;
 (b) a dispersive element for separating the light collimated by said second lens into its component wavelengths; and
 (c) a second lens for focusing the dispersed light produced by said element.

8. A reflection spectrophotometer according to claim 7 wherein said dispersive element comprises a reflective diffraction grating.

9. A reflection spectrophotometer with parallel sensing for analyzing the light diffusely reflected by a sample comprising:
 (a) a pulsed xenon flashtube;
 (b) means for diffusing the light emitted by said flashtube;
 (c) illumination optics for uniformly illuminating said sample with said diffuse light from a complete annular ring at a small angular spread about 45° to said sample, said illumination optics comprising an annular reflective surface for deflecting said diffuse light toward said sample from a complete annular ring at an angular spread about 45° to said sample and a set of annular baffles for limiting the spread of said diffuse light to a small angle about 45° to the sample normal;
 (d) collection optics for collecting said diffuse light reflected from said sample at a small angular spread about the normal to said sample, said collection optics comprising a lens for collecting and focusing the light diffusely reflected from said sample at a small angular spread about the normal to said sample and means for transmitting the light collected and focused by said lens;
 (e) means for focusing the light collected by said collection optics;
 (f) a slit responsive to said focused light for restricting the angular spread thereof;
 (g) means responsive to the light passed by said slit for separating said light into its component wavelengths and for focusing the dispersed light; and
 (h) an array of discrete photodetectors located in the plane of the focused spectrum and responsive thereto for simultaneously sensing the energy present at said component wavelengths.

* * * * *